United States Patent [19]

Fey et al.

[11] Patent Number: 5,594,010

[45] Date of Patent: Jan. 14, 1997

[54] SUBSTITUTED MONOPYRIDYLMETHYL DERIVATIVES

[75] Inventors: Peter Fey; Thomas Krämer, both of Wuppertal; Jürgen Dressel, Radevormwald; Rudolf Hanko, Essen; Walter Hübsch; Ulrich Müller, both of Wuppertal; Matthias Müller-Gliemann, Solingen; Martin Beuck, Erkrath; Hilmar Bischoff, Wuppertal; Stefan Wohlfeil, Hilden; Dirk Denzer; Stanislav Kazda, both of Wuppertal; Johannes-Peter Stasch, Solingen; Andreas Knorr, Erkrath; Siegfried Zaiss, Wuppertal, all of Germany

[73] Assignee: Bayer Aktiengesellschaft, Leverkusen, Germany

[21] Appl. No.: 262,085

[22] Filed: Jun. 17, 1994

[30] Foreign Application Priority Data

Jun. 21, 1993 [DE] Germany ............... 43 20 432.5

[51] Int. Cl.$^6$ .................... A61K 31/44; C07D 401/14
[52] U.S. Cl. .................... 514/340; 546/268.4; 546/274.7; 546/275.1; 546/118
[58] Field of Search ................... 546/118, 274.7, 546/275.1, 268.4; 514/340

[56] References Cited

U.S. PATENT DOCUMENTS 5,128,327  7/1992  Chakravarty et al. .................. 546/118
5,283,242  2/1994  Ellingboe ............................... 514/186
5,328,911  7/1994  Miyake et al. ......................... 546/118
5,389,634  2/1995  Fortin et al. ........................... 514/248

FOREIGN PATENT DOCUMENTS 0400974  5/1990  European Pat. Off. .
0533058  9/1991  European Pat. Off. .
0499415  2/1992  European Pat. Off. .
0510813  3/1992  European Pat. Off. .
0508393  4/1992  European Pat. Off. .
0503393  9/1992  European Pat. Off. .
0504888  9/1992  European Pat. Off. .
0508445  10/1992  European Pat. Off. .
0518033  12/1992  European Pat. Off. .

OTHER PUBLICATIONS

The Journal of Cell Biology, vol. 50, 1971, pp. 172–186; "The Smooth Muscle Cell", R. Ross.

Biorganic & Medical Chemistry Letters, vol. 3, No. 6, 1993, pp. 1055–1060.

J. Med. Chem. vol. 36, Martin Winn et al., pp. 2676–2688, 1993.

Primary Examiner—Bernard Dentz
Attorney, Agent, or Firm—Sprung Horn Kramer & Woods

[57] ABSTRACT

The substituted monopyridyl and bipyridyl derivatives are prepared by reacting substituted pyridine halides with phenylboronic acids. They are suitable for use as active compounds in medicaments for treating arterial hypertension and atherosclerosis.

7 Claims, No Drawings

SUBSTITUTED MONOPYRIDYLMETHYL DERIVATIVES

The invention relates to substituted monopyridylmethyl and bipyridylmethyl derivatives, to a process for their preparation and to their use in medicaments, in particular as hypotensive and anti-atherosclerotic agents.

It is known that renin, a proteolytic enzyme, cleaves angiotensinogen in vivo to give the decapeptide angiotensin I, which, in turn, is broken down in the lungs, the kidneys and other tissues to the octapeptide vasopressor angiotensin II. The various effects of angiotensin II, such as, for example, vasoconstriction, $Na^+$ retention in the kidney, aldosterone liberation in the adrenal gland, and increase in the tone of the sympathetic nervous system, act synergistically to increase blood pressure.

In addition to this, angiotensin II possesses the property of promoting the growth and multiplication of cells, such as, for example, cardiac muscle cells and smooth muscle cells, causing these cells to grow to an increased extent and to proliferate in various disease states (e.g. hypertension, atherosclerosis and cardiac insufficiency).

One possible approach to intervention in the reninangiotensin system (RAS), other than inhibition of renin activity, is to inhibit the activity of the angiotensin-converting enzyme (ACE) and to blockade angiotensin II receptors.

Arylheteroarylalkyl-substituted triazoles and imidazoles are known from the publications EP 508 445, EP 503 393, EP 504 888 and U.S. Pat. No. 5,128,327 to be A II-antagonists.

In addition, condensed heterocycles having an A II-antagonistic effect are described in EP 518 033 Al.

The present invention relates to substituted monopyridylmethyl and bipyridylmethyl derivatives of the general formula (I)

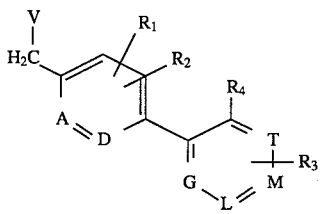

in which

A, D, G, L, M and T are identical or different and represent the CH group or represent a nitrogen atom, where, however, at least one of these radicals, and, maximally, in each case one of these radicals in each cycle, must/may represent a nitrogen atom, V represents a radical of the formula

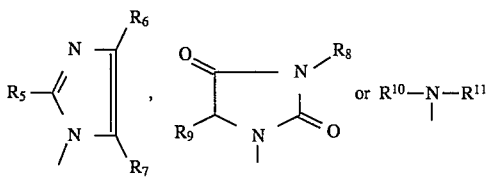

in which $R^5$, $R^8$ and $R^9$ are identical or different and denote straight-chain or branched alkyl having up to 10 carbon atoms which is optionally substituted by cycloalkyl having 3 to 6 carbon atoms, by hydroxyl, or by straight-chain or branched alkoxy or alkylthio having in each case up to 6 carbon atoms, or denote cycloalkyl having 3 to 6 carbon atoms, $R^6$ denotes halogen, $R^7$ denotes formyl, carboxyl, straight-chain or branched alkoxycarbonyl having up to 6 carbon atoms, or straight-chain or branched alkyl having up to 6 carbon atoms which is optionally substituted by hydroxyl, or $R^6$ and $R^7$, with the inclusion of the double bond, together form a pyridyl ring which is substituted identically or differently 2 to 3 times by carboxyl, straight-chain or branched alkoxycarbonyl having up to 6 carbon atoms, or by straight-chain or branched alkyl having up to 6 carbon atoms which, for its part, can be substituted by hydroxyl, $R^{10}$ denotes straight-chain or branched alkyl having up to 8 carbon atoms, cycloalkyl having 3 to 6 carbon atoms, or straight-chain or branched acyl having up to 8 carbon atoms which is optionally substituted by straight-chain or branched acyl having up to 8 carbon atoms, $R^{11}$ denotes pyridyl which is optionally substituted identically or differently up to 2 times by carboxyl, straight-chain or branched alkoxycarbonyl having up to 6 carbon atoms, or by straight-chain or branched alkyl having up to 6 carbon atoms which, for its part, can be substituted by hydroxyl, or denotes straight-chain or branched alkyl having up to 8 carbon atoms which is optionally substituted by carboxyl or by straight-chain or branched alkoxycarbonyl having up to 6 carbon atoms, or denotes a group of the formula $-CO-NR^{12}R^{13}$, in which $R^{12}$ denotes hydrogen or methyl, $R^{13}$ denotes straight-chain or branched alkyl having up to 8 carbon atoms which is substituted by carboxyl or straight-chain or branched alkoxycarbonyl having up to 6 carbon atoms, $R^1$, $R^2$ and $R^3$ are identical or different and represent hydrogen, halogen, cyano, nitro, trifluoromethyl or amido, or represent straight-chain or branched alkyl or alkoxycarbonyl having up to 6 carbon atoms, $R^4$ represents a group of the formula $-CO-R^{14}$, $-SO_2R^{15}$, $-CO-NR^{16}R^{17}$, $-NH-SO_2R^{18}$ or $-SO_2NR^{19}R^{20}$, in which $R^{14}$ denotes hydroxyl or straight-chain or branched alkoxy having up to 6 carbon atoms, $R^{15}$ denotes hydroxyl, trifluoromethyl, straight-chain or branched alkoxy or alkyl having in each case up to 6 carbon atoms, phenyl or benzyl which are optionally substituted identically or differently up to 2 times by halogen, trifluoromethyl or straight-chain or branched alkyl having up to 4 carbon atoms, $R^{16}$ and $R^{17}$ are identical or different and denote hydrogen, cycloalkyl having 3 to 8 carbon atoms, or straight-chain or branched alkyl having up to 8 carbon atoms which is optionally substituted by phenyl, or $R^{16}$ denotes hydrogen and $R^{17}$ denotes the group $-SO_2R^{15}$, in which $R^{15}$ has the abovementioned meaning, $R^{18}$ has the abovementioned meaning of $R^{15}$ and is identical to or different from the latter, $R^{19}$ and $R^{20}$ have the abovementioned meaning of $R^{16}$ and $R^{17}$ and are identical to or difference from the latter, or $R^{19}$ denotes hydrogen or straight-chain or branched alkyl having up to 4 carbon atoms, and $R^{20}$ has the abovementioned meaning of $R^{15}$ and is identical to or different from the latter, or $R^4$ represents a radical of the formula

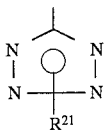

in which $R^{21}$ denotes hydrogen or straight-chain or branched alkyl having up to 8 carbon atoms which is optionally substituted by straight-chain or branched acyl having up to 6 carbon atoms, or denotes the triphenylmethyl group, and salts thereof.

The substituted monopyridylmethyl and bipyridylmethyl derivatives may also be present in the form of their salts. In this connection, salts with organic or inorganic bases or acids may be mentioned in a general manner.

Within the scope of the present invention, physiologically harmless salts are preferred. Physiologically harmless salts of the compounds according to the invention can be salts of the substances according to the invention with mineral acids, carboxylic acids or sulphonic acids. Examples which are particularly preferred are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically harmless salts may also be metal or ammonium salts of the compounds according to the invention which possess a free carboxyl group or a tetrazolyl radical. Examples of those salts which are particularly preferred are sodium, potassium, magnesium or calcium salts, and ammonium salts which are derived from ammonia, or organic amines, such as, for example, ethylamine, diethylamine or triethylamine, diethanolamine or triethanolamine, dicyclohexylamine, dimethylaminoethanol, arginine, lysine, ethylenediamine or 2-phenylethylamine.

The compounds according to the invention can exist in stereoisomeric forms which either do (enantiomers) or do not (diastereomers) relate to each other as image and mirror image. The invention relates to the enantiomers or diastereomers or their respective mixtures. The racemic forms and the diastereomeric mixtures can be resolved in a known manner into their stereoisomerically homogeneous constituents [cf. E. L. Eliel, Stereochemistry of Carbon Compounds, McGraw Hill, 1962].

Compounds of the general formula (I) are preferred in which

A, D, G, L, M and T are identical or different and represent the CH group or a nitrogen atom, where, however, at least one of the radicals, and, maximally, in each case one of the radicals in each cycle, must/may represent a nitrogen atom, V represents a radical of the formula

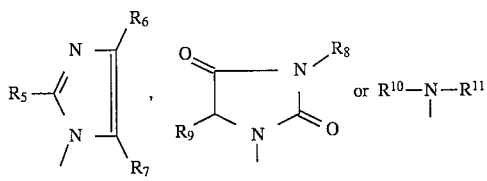

in which $R^5$, $R^8$ and $R^9$ are identical or different and denote straight-chain or branched alkyl having, in each case up to 8 carbon atoms which is optionally substituted by cyclopropyl, cyclopentyl, cyclohexyl or hydroxyl, or by straight-chain or branched alkoxy or alkylthio having in each case up to 4 carbon atoms, or denote cyclopropyl, cyclopentyl or cyclohexyl, $R^6$ denotes fluorine, chlorine or bromine, $R^7$ denotes formyl, carboxyl, straight-chain or branched alkoxycarbonyl having up to 4 carbon atoms, or straight-chain or branched alkyl having up to 4 carbon atoms which is optionally substituted by hydroxyl, or $R^6$ and $R^7$, with the inclusion of the double bond, together form a pyridyl ring which is substituted identically or differently 2 to 3 times by carboxyl, by straight-chain or branched alkoxycarbonyl having up to 4 carbon atoms, or by straight-chain or branched alkyl having up to 4 carbon atoms which, for its part, can be substituted by hydroxyl, $R^{10}$ denotes straight-chain or branched alkyl having up to 6 carbon atoms, cyclopropyl, cyclopentyl or cyclohexyl, or straight-chain or branched acyl having up to 6 carbon atoms which is optionally substituted by straight-chain or branched acyl having up to 6 carbon atoms, $R^{11}$ denotes pyridyl which is optionally substituted identically or differently up to 2 times by carboxyl, by straight-chain or branched alkoxycarbonyl having up to 4 carbon atoms, or by straight-chain or branched alkyl having up to 4 carbon atoms which, for its part, can be substituted by hydroxyl, or denotes straight-chain or branched alkyl having up to 6 carbon atoms which is optionally substituted by carboxyl or by straight-chain or branched alkoxycarbonyl having up to 4 carbon atoms, or denotes a group of the formula —CO—NR$^{12}$R$^{13}$, in which $R^{12}$ denotes hydrogen or methyl, $R^{13}$ denotes straight-chain or branched alkyl having up to 6 carbon atoms which is substituted by carboxyl or by straight-chain or branched alkoxycarbonyl having up to 4 carbon atoms, $R^1$, $R^2$ and $R^3$ are identical or different and represent hydrogen, fluorine, chlorine, bromine, trifluoromethyl or amido, or represent straight-chain or branched alkyl or alkoxycarbonyl having in each case up to 4 carbon atoms, $R^4$ represents a group of the formula —CO—R$^{14}$, —SO$_2$R$^{15}$, —CO—NR$^{16}$R$^{17}$, —NH—SO$_2$R$^{18}$ or —SO$_2$NR$^{19}$R$^{20}$, in which $R^{14}$ denotes hydroxyl or straight-chain or branched alkoxy having up to 4 carbon atoms, $R^{15}$ denotes straight-chain or branched alkyl having up to 4 carbon atoms, benzyl, trifluoromethyl or p-tolyl, $R^{16}$ and $R^{17}$ are identical or different and denote hydrogen, cyclopropyl, cyclopentyl or cyclohexyl, or straight-chain or branched alkyl having up to 6 carbon atoms which is optionally substituted by phenyl, or $R^{16}$ denotes hydrogen, and $R^{17}$ denotes the group —SO$_2$R$^{15}$, in which $R^{15}$ has the abovementioned meaning, $R^{18}$ has the abovementioned meaning of $R^{15}$ and is identical to or different from the latter, $R^{19}$ and $R^{20}$ have the abovementioned meaning of $R^{16}$ and $R^{17}$ and are identical to or different from the latter, or $R^{19}$ denotes hydrogen or methyl, $R^{20}$ has the abovementioned meaning of $R^{15}$ and is identical to or different from the latter, or $R^4$ represents a radical of the formula

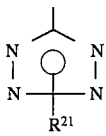

in which $R^{21}$ denotes hydrogen or straight-chain or branched alkyl having up to 6 carbon atoms which is optionally substituted by straight-chain or branched acyl having up to 4 carbon atoms, or denotes the triphenylmethyl group, and salts thereof.

Compounds of the general formula (I) are particularly preferred in which

A, D, G, L, M and T are identical or different and represent the CH group or represent a nitrogen atom, where, however, at least one of the radicals, and, maximally, in each case one of the radicals in each cycle, must/may represent a nitrogen atom, V represents a radical of the formula

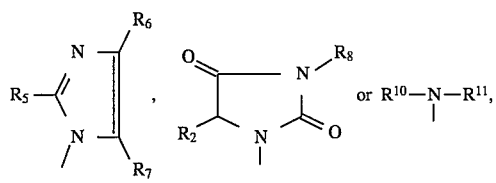

in which $R^5$, $R^8$ and $R^9$ are identical or different and denote straight-chain or branched alkyl having up, to 6 carbon atoms which is optionally substituted by cyclopropyl or hydroxyl, or by straight-chain or branched alkoxy or alkylthio having in each case up to 3 carbon atoms, or denote cyclopropyl, chlorine or iodine, $R^6$ denotes fluorine, chlorine or bromine, $R^7$ denotes formyl, carboxyl, straight-chain or branched alkoxycarbonyl having up to 3 carbon atoms, or straight-chain or branched alkyl having up to 4 carbon atoms which is optionally substituted by hydroxyl, or $R^6$ and $R^7$, with the inclusion of the double bond, together form a pyridyl ring which is substituted identically or differently 2 or 3 times by carboxyl, by straight-chain or branched alkoxycarbonyl having up to 3 carbon atoms, or by straight-chain or branched alkyl having up to 3 carbon atoms which, for its part, can be substituted by hydroxyl, $R^{10}$ denotes straight-chain or branched alkyl having up to 5 carbon atoms, cyclopropyl, cyclopentyl or cyclohexyl, or straight-chain or branched acyl having up to 5 carbon atoms which is optionally substituted by straight-chain or branched acyl having up to 5 carbon atoms, $R^{11}$ denotes pyridyl which is optionally substituted identically or differently up to 2 times by carboxyl, by straight-chain or branched alkoxycarbonyl having up to 3 carbon atoms, or by straight-chain or branched alkyl having up to 3 carbon atoms which, for its part, can be substituted by hydroxyl, or denotes straight-chain or branched alkyl having up to 5 carbon atoms which is optionally substituted by carboxyl or by straight-chain or branched alkoxycarbonyl having up to 3 carbon atoms, or denotes a group of the formula —CO—$NR^{12}R^{13}$, in which $R^{12}$ denotes hydrogen or methyl, $R^{13}$ denotes straight-chain or branched alkyl having up to 6 carbon atoms which is substituted by carboxyl or by straight-chain or branched alkoxycarbonyl having up to 3 carbon atoms, $R^1$, $R^2$ and $R^3$ are identical or different and represent hydrogen, fluorine, chlorine, bromine or methyl, $R^4$ denotes a group of the formula —CO—$R^{14}$, —$SO_2R^{15}$, —CO—$NR^{16}R^{17}$, —NH—$SO_2R^{18}$ or —$SO_2NR^{19}R^{20}$, in which $R^{14}$ denotes hydroxyl or straight-chain or branched alkoxy having up to 3 carbon atoms, $R^{15}$ denotes methyl, trifluoromethyl, benzyl or p-tolyl, $R^{16}$ and $R^{17}$ are identical or different and denote hydrogen, cyclopropyl or cyclopentyl, or straight-chain or branched alkyl having up to 4 carbon atoms which is optionally substituted by phenyl, $R^{16}$ denotes hydrogen, and $R^{17}$ denotes the group —$SO_2$—$R^{15}$, in which $R^{15}$ has the abovementioned meaning, $R^{18}$ has the abovementioned meaning of $R^{15}$ and is identical to or different from the latter, $R^{19}$ and $R^{20}$ have the abovementioned meaning of $R^{16}$ and $R^{17}$ and are identical to or different from the latter, or $R^{19}$ denotes hydrogen or methyl, and $R^{20}$ has the abovementioned meaning of $R^{15}$ and is identical to or different from the latter, or $R^4$ represents the tetrazolyl radical of the formula

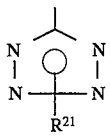

in which $R^{21}$ denotes hydrogen or straight-chain or branched alkyl having up to 4 carbon atoms which is optionally substituted by straight-chain or branched acyl having up to 4 carbon atoms, or denotes the triphenylmethyl group, and salts thereof.

Compounds of the general formula (I) are very particularly preferred in which

A or D represents a nitrogen atom and the other radical in each case represents the CH group, G, L, M and T represent the CH group, V represents a radical of the formula

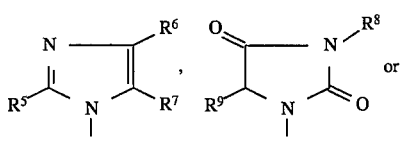

$R^{10}-N-R^{11}$, in which $R^5$, $R^8$ and $R^9$ are identical or different and denote straight-chain or branched alkyl having up to 6 carbon atoms, or cyclopropyl, $R^6$ denotes fluorine, chlorine or bromine, $R^7$ denotes formyl, carboxyl, methoxycarbonyl or ethoxycarbonyl, or hydroxymethyl, or $R^6$ and $R^7$, with the inclusion of the double bond, together form a pyridyl radical which can be substituted up to 2 times by bromine or methyl, $R^{10}$ denotes straight-chain or branched alkyl having up to 5 carbon atoms, or denotes straight-chain or branched acyl having up to 5 carbon atoms which is optionally substituted by acyl having up to 5 carbon atoms, $R^{11}$ denotes pyridyl which can be substituted by carboxyl or by alkoxycarbonyl having up to 3 carbon atoms, or denotes straight-chain or branched alkyl having up to 5 carbon atoms which can be substituted by carboxyl or alkoxycarbonyl having up to 3 carbon atoms, or denotes a group of the formula $-CO-NR^{12}R^{13}$, in which $R^{12}$ denotes hydrogen or methyl $R^{13}$ denotes straight-chain or branched alkyl having up to 6 carbon atoms which is substituted by carboxyl or by alkoxycarbonyl having up to 3 carbon atoms, $R^1$, $R^2$ and $R^3$ represent hydrogen, $R^4$ represents a tetrazolyl radical of the formula $$\begin{array}{c} \\ N \diagup \diagdown N \\ | \phantom{xxx} | \\ N-\!\!\!\!-\!\!\!\!-N \\ | \\ R^{21} \end{array}$$

in which $R^{21}$ denotes hydrogen or the triphenylmethyl group, and salts thereof.

In addition, a process has been found for preparing the compounds of the general formula (I) according to the invention, which process is characterized in that compounds of the general formula (II)

$$\text{(II)}$$

in which

A, D, V, $R^1$ and $R^2$ have the abovementioned meaning, and $R^{22}$ represents a typical leaving group, such as, for example, bromine, iodine, methanesulphonyloxy, toluenesulphonyloxy, fluorosulphonyloxy or trifluoromethanesulphonyloxy, preferably bromine, are reacted with compounds of the general formulae (III) or (IIIa)

$$\text{(III)}$$

$$\text{(IIIa)}$$

in which

G, L, M, T and $R^3$ have the abovementioned meaning, $R^{21'}$ represents hydrogen or represents the triphenylmethyl group, and $R^{23}$ has the abovementioned meaning of $R^4$ but does not represent the tetrazolyl substituent, in inert solvents, in the presence of a base and with catalysis by a metal, and subsequently, in the case where $R^{21'}$=triphenylmethyl group, this group is eliminated under customary conditions using acids in organic solvents and/or water, and, in the case of the salts, reaction takes place with acids or bases, preferably starting from the free tetrazole ($R^{21}/R^{21'}$=H, and, in the case of the free acid $R^4$=$CO_2H$ and the free tetrazole $R^{21}/R^{21'}$=H, reaction takes place with acids, starting from the salts, and, in the case of the carboxylic radicals listed under the $R^4$ substituents, derivatization optionally takes place in accordance with customary methods, for example by amidation or sulphoamidation, following hydrolysis of the respective esters, and the substituents are optionally varied at each step of the process in accordance with known methods.

The process according to the invention may be illustrated, by way of example, by the following formula scheme

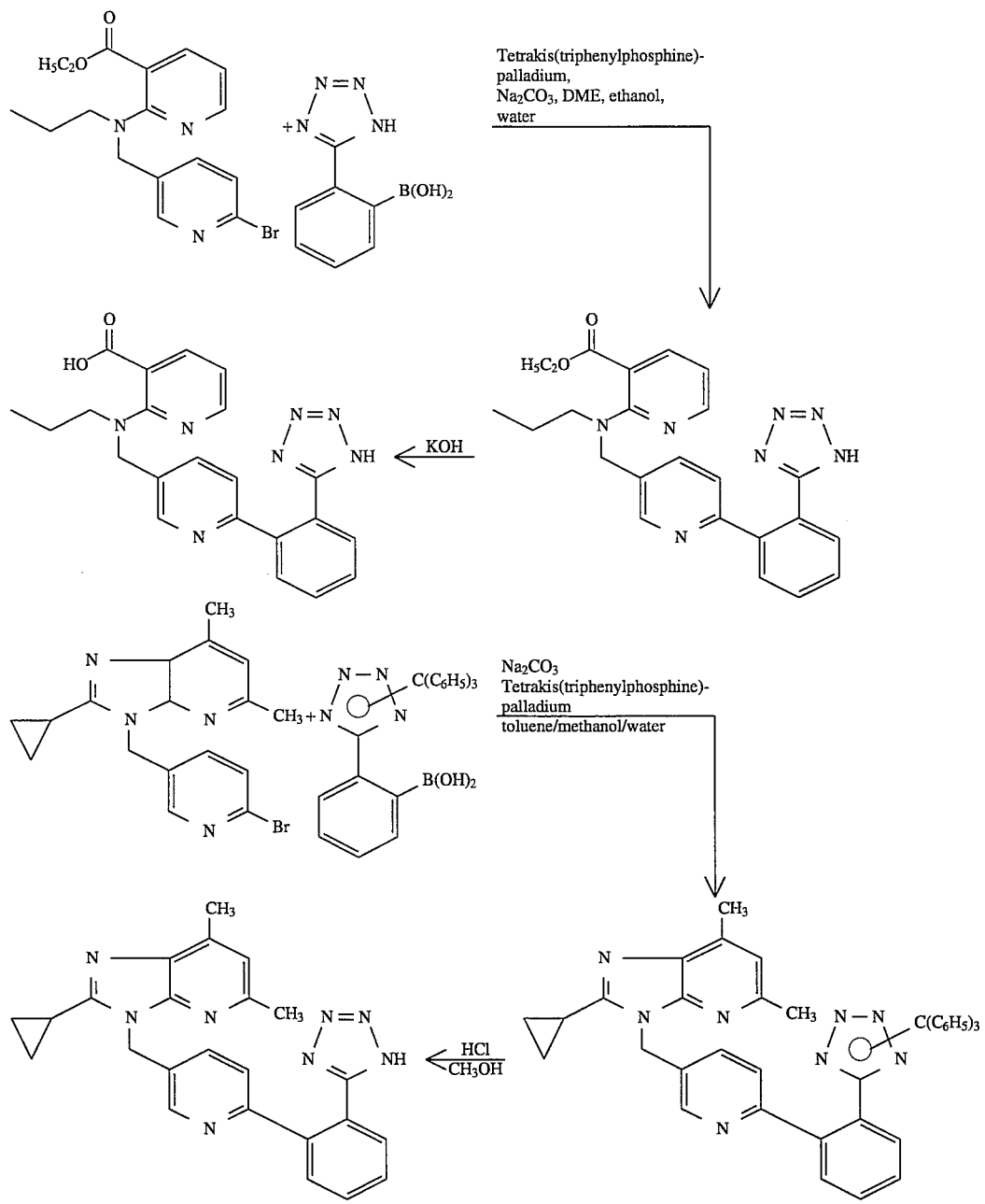

Customary organic solvents, which are not altered under the reaction conditions, are suitable for use as solvents for the process. These preferably include water or alcohols, such as, for example, methanol, ethanol and propanol, ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, dimethyl sulphoxide, dimethylformamide or dimethoxyethane, hexamethylphosphoric triamide, acetonitrile, acetone or nitromethane. It is also possible to use mixtures of the said solvents. Tetrahydrofuran, acetone, dimethylformamide, dimethoxyethane, toluene and methanol/water are preferred.

In general, inorganic or organic bases can be employed as bases for the process according to the invention. These preferably include alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate or cesium carbonate, or alkali metal or alkaline earth metal alcoholates or amides, such as sodium or potassium methanolate, sodium or potassium ethanolate, or potassium tertbutylate, thallium carbonate or hydroxide, or lithium diisopropylamide (LDA), or organic amines (trialkyl($C_1$–$C_6$)amines), such as triethylamine or diisopropylethylamine, or heterocycles, such as 1,4-diazabicyclo[2.2.2]octane (DABCO), 1,8-diazabicyclo[5.4.0]undec-7-ene, (DBU), pyridine, dimethylaminopyridine, methylpiperidine or morpholine. It is also possible to employ alkali metals, such as sodium, or their hydrides, such as sodium hydride, as bases. Potassium carbonate, sodium carbonate, sodium hydride, potassium tert-butylate, cesium carbonate, thallium hydroxide and thallium carbonate are preferred.

In general, the base is employed in a quantity of from 0.05 mol to 10 mol, preferably of from 1 mol to 2 mol, in each case based on 1 mol of the compound of the formula (III).

The processes according to the invention are generally carried out in a temperature range of from −100° C. to 100° C., preferably of from 0° C. to 80° C., and in a protective gas atmosphere.

In general, metal complexes of nickel, palladium or platinum, preferably palladium(O) complexes, such as, for example, tetrakis(triphenylphosphine)palladium, are suitable for use as catalysts. It is also possible to use phase-transfer catalysts, such as, for example, tetra-n-butylammonium bromide or crown ether.

Potassium or sodium iodide, preferably sodium iodide, are also suitable for use as catalysts.

The catalyst is employed in a quantity of from 0.005 mol to 0.2 mol, preferably of from 0.01 mol to 0.05 mol, based on 1 mol of the compound of the general formula (III) or (IIIa).

The process according to the invention is generally carried out under atmospheric pressure. However, it is also possible to carry out the process at elevated pressure or reduced pressure (e.g. in a range of from 0.5 to 5 bar).

The triphenylmethyl group is eliminated using acetic acid or trifluoroacetic acid and water or one of the above-listed alcohols, or using aqueous hydrochloric acid in the presence of acetone or likewise with alcohols.

The elimination is generally effected in a temperature range of from 0° C. to 150° C., preferably of from 20° C. to 100° C., and under atmospheric pressure.

The alkylation is generally effected using alkylating agents, such as, for example, ($C_1$–$C_{10}$)-alkyl halides, sulphonic esters, or substituted or unsubstituted ($C_1$–$C_{10}$)-dialkylsulphonates or ($C_1$–$C_{10}$)-diarylsulphonates, preferably methyl iodide or dimethyl sulphate.

In general, the alkylation is effected in one of the above-listed solvents, preferably in dimethylformamide, in a temperature range of from 0° C. to +70° C., preferably of from 0° C. to +30° C., and under atmospheric pressure.

The customary inorganic bases can suitably be used as bases for the hydrolysis. These preferably include alkali metal hydroxides or alkaline earth metal hydroxides, such as, for example, sodium hydroxide, potassium hydroxide or barium hydroxide, or alkali metal carbonates, such as sodium or potassium carbonate or sodium hydrogen carbonate, or alkali metal alcoholates, such as sodium methanolate, sodium ethanolate, potassium methanolate, potassium ethanolate or potassium tert-butanolate. Sodium hydroxide or potassium hydroxide are particularly preferably employed.

Water, or the customary organic solvents for a hydrolysis, can suitably be used as solvents for the hydrolysis. These organic solvents preferably include alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of said solvents.

Where appropriate, the hydrolysis can also be carried out using acids, such as, for example, trifluoroacetic acid, acetic acid, hydrochloric acid, hydrobromic acid, methanesulphonic acid, sulphuric acid or perchloric acid, preferably using trifluoroacetic acid.

In general, the hydrolysis is carried out in a temperature range of from 0° C. to +100° C., preferably of from +20° C. to +80° C.

In general, the hydrolysis is carried out under atmospheric pressure. However, it is also possible to carry it out under reduced pressure or under excess pressure (e.g. from 0.5 to 5 bar).

When carrying out the hydrolysis, the base is generally employed in a quantity of from 1 to 3 mol, preferably of from 1 to 1.5 mol, based on 1 mol of the ester. Molar quantities of the reactants are particularly preferably used.

In general, tert-butyl esters are hydrolysed using acids, such as, for example, hydrochloric acid or trifluoroacetic acid, in the presence of one of the abovementioned solvents and/or water, or their mixtures, preferably with dioxane or tetrahydrofuran.

In general, the amidation and the sulphonamidation are effected in one of the above-listed solvents, preferably in tetrahydrofuran or dichloromethane.

Where appropriate, the amidation and the sulphonamidation can proceed via the activated step of the acid halides, which can be prepared from the corresponding acids by reaction with thionyl chloride, phosphorus trichloride, phosphorus pentachloride, phosphorus tribromide or oxalyl chloride.

In general, the amidation and the sulphonamidation are effected in a temperature range of from −20° C. to +80° C., preferably of from −10° C. to +30° C. and under atmospheric pressure.

In addition to the above-listed bases, triethylamine and/or dimethylaminopyridine, DBU or DABCO can suitably be used as bases for this purpose.

The base is employed in a quantity of 0.5 mol to 10 mol, preferably of 1 mol to 2 mol, based on 1 mol of the corresponding acid or ester.

Alkali metal or alkaline earth metal carbonates, such as sodium carbonate or potassium carbonate, alkali metal or alkaline earth metal hydroxides, such as, for example, sodium or potassium hydroxide, or organic bases, such as pyridine, triethylamine or N-methylpiperidine, or bicyclic amidines, such as 1,5-diazabicyclo[4.3.0]non-5-ene (DBN) or 1,8-diazabicyclo[5.4.0]undec-7-ene (DBU) can be employed as acid-binding agents for the sulphonamidation. Potassium carbonate is preferred.

Suitable dehydrating reagents are carbodiimides, such as, for example, diisopropylcarbodiimide, dicyclohexylcarbodiimide, or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium-3-sulphonate, or propanephosphoric anhydride, or isobutylchloroformate, or benzotriazolyloxy-tris-(dimethylamino)phosphonium hexafluorophosphate, or diphenylphosporyl azide, or methanesulphonyl chloride, optionally in the presence of bases, such as triethylamine, or N-ethylmorpholine, or N-methylpiperidine or dicyclohexylcarbodiimide, and N-hydroxysuccinimide.

In general, the acid-binding agents and dehydrating reagents are employed in a quantity of from 0.5 to 3 mol, preferably of from 1 to 1.5 mol, based on 1 mol of the corresponding carboxylic acids.

For the most part, the compounds of the general formula (II) are novel and can be prepared, for example, by, in the case where V represents the radical of the formula

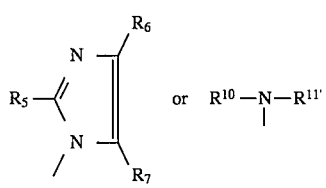

in which

R$^5$, R$^6$, R$^7$ and R$^{10}$ have the abovementioned meaning, and

R$^{11'}$ represents the optionally substituted pyridine listed above under R$^{11}$, either reacting compounds of the general formula (IV) or (V)

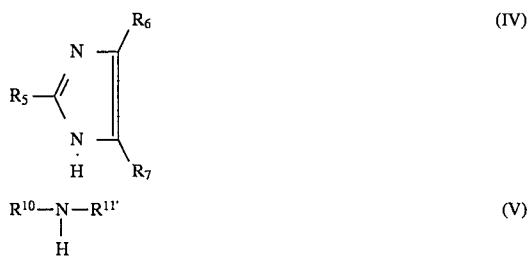

in which

R$^5$, R$^6$, R$^7$ and R$^{11'}$ have the abovementioned meaning, with compounds of the general formula (VI)

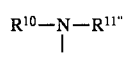

in which

A, D, R$^1$, R$^2$ and R$^{22}$ have the abovementioned meaning, and

R$^{24}$ represents halogen, preferably bromine, in one of the above-listed solvents and the bases there-described, preferably dimethyl sulphoxide and sodium hydride, and, in the case where V represents the radical of the formula

in which

R$^{10}$ has the abovementioned meaning and

R$^{11''}$ has the abovementioned meaning of R$^{11}$, but does not represent optionally substituted pyridyl, initially converting compounds of the general formula

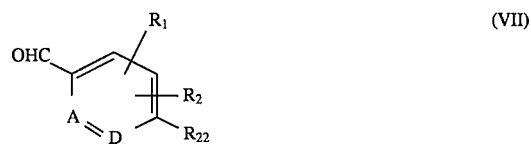

in which

A, D, R$^1$, R$^2$ and R$^{22}$ have the abovementioned meaning, by reductive amination in accordance with known methods using amines of the general formula (VIII)

$$H_2N—R^{25} \quad (VIII)$$

in which

R$^{25}$ encompasses the respective abovementioned scope of meaning of R$^{10}$ or R$^{11''}$, in one of the above-listed solvents, optionally in the presence of a base, into the compounds of the general formula (IX)

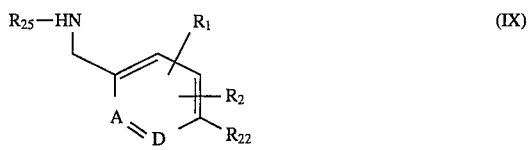

in which

A, D, R$^1$, R$^2$, R$^{22}$ and R$^{25}$ have the abovementioned meaning, and, in a last step, reacting with isocyanates of the general formula (X)

$$R^{26}—N=C=O \quad (X)$$

in which

R$^{26}$, in dependence on the above-listed scope of meaning of the substituent R$^{25}$ encompasses the above-mentioned scope of meaning of either R$^{10}$ or R$^{11''}$.

In general, the processes according to the invention are carried out in a temperature range of from −100° C. to 100° C., preferably of from 0° C. to 80° C., and in a protective gas atmosphere.

In general, the process according to the invention is carried out under atmospheric pressure. However, it is also possible to carry out the process under excess pressure or under reduced pressure (e.g. in a range of from 0.5 to 5 bar).

The compounds of the general formula (IV), (V), (VI), (VII), (VIII) and (X) are known or else can be prepared by known methods.

The compounds of the general formula (IX) are known or else can be prepared as described above, for example.

The compounds of the general formula (II), in which V represents the radical of the formula

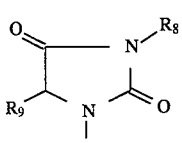

are likewise novel and can, for example, be prepared by first converting compounds of the general formula (XI) in which

R$^9$ has the above-mentioned meaning, and

Z represents C$_1$-C$_4$-alkoxy, by reaction with compounds of the general formula (VI) as described above, into the compounds of the general formula (XII)

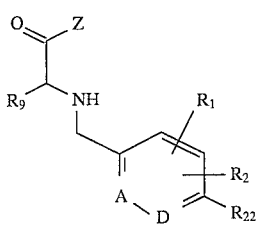

(XII)

in which
R$^1$, R$^2$, R$^9$, R$^{22}$, A, D and Z have the abovementioned meaning, and, in a last step, reacting with isocyanates of the general formula (XIII)

  (XIII)

in which
R$^8$ has the abovementioned meaning, in inert solvents and in the presence of an acid.

In general, the first stage of the process is effected in one of the above-listed solvents and bases, preferably dimethylformamide or dichloromethane, triethylamine and potassium tert-butylate, in a temperature range of from 0° C. to 100° C., preferably at room temperature, and under atmospheric pressure. In general, the reaction is carried out under a protective gas atmosphere.

In general, the reaction with the isocyanates is effected in ethyl acetate and protonic acid, preferably using hydrochloric acid in a temperature range of from 0° C. to 100° C., preferably of from 60° C. to 80° C., and under atmospheric pressure.

The compounds of the general formula (XI) are known or can be prepared by known methods.

The compounds of the general formula (XIII) are likewise known.

The compounds of the general formula (XII) are novel and can be prepared as described above.

The compounds of the general formula (III) are known, but novel in the case where R$^{21}$=H, and can then be prepared by first reacting phenyltetrazole under a protective gas atmosphere in an aprotic solvent and in the presence of a base, and then adding trimethyl borate, and, in a last step, hydrolysing with acids.

Aprotic solvents, such as ethers, for example tetrahydrofuran or diethyl ether, toluene, hexane or benzene can suitably be used as solvent for the process. Tetrahydrofuran is preferred.

Suitable bases are prim-, sec- and tert-butyllithium and phenyllithium. n-Butyllithium is preferred.

The base is employed in a quantity of from 2 mol to 5 mol, preferably of from 2 mol to 3 mol, based on 1 mol of phenyltetrazole.

In general, suitable acids are mineral acids, such as, for example, hydrochloric acid, C$_1$–C$_4$-carboxylic acids, such as, for example, acetic acid, or phosphoric acids. Hydrochloric acid is preferred.

In general, the acid is employed in a quantity of from 1 mol to 10 mol, preferably of from 1 mol to 3 mol.

In general, the process is carried out in a temperature range of from –70° C. to +25° C., preferably at from –10° C. to 0° C.

In general, the process according to the invention is carried out under atmospheric pressure. However, it is also possible to carry out the process under elevated pressure or under reduced pressure (e.g. in a range of from 0.5 to 5 bar).

The above preparation processes are given solely for clarification. The preparation of the compounds of the general formula (I) according to the invention is not limited to these processes, and any modification of these processes is applicable to the preparation in the same way.

The substituted monopyridylmethyl and bipyridylmethyl derivatives according to the invention exhibit a valuable spectrum of pharmacological activity which could not have been foreseen.

The compounds according to the invention possess a specific A II-antagonistic effect, since they competitively inhibit the binding of angiotensin II to the receptors. They suppress the vasoconstrictive and aldosterone secretion-stimulating effects of angiotensin II. In addition to this, they inhibit the proliferation of smooth muscle cells.

They can, therefore, be employed in medicaments for treating arterial hypertension and atherosclerosis. In addition to this, they can be employed for treating coronary heart diseases, cardiac insufficiency, disturbances of cerebral function, ischaemic brain disorders, disturbances of peripheral blood flow, functional disturbances of the kidney and adrenal gland, disorders of the respiratory system of bronchospastic and vascular origin, sodium retention and oedemas.

The compounds can also be used for the control of glaucoma, diabetic retinopathy and increases in the mobility of the intraocular retinal fluid.

They are also suitable for controlling diseases of the central nervous system such as for example depression, migraine, schizophrenia or anxiety states, brain dysfunctions, strokes, diabetic nephropathy, cardiac dysrhythmias, or for the prophylaxis of coronary heart diseases or restenosis after angioplasty and vascular surgery.

Investigation of the inhibition of agonist-induced contraction

Rabbits of both sexes are rendered unconscious by a blow to the neck and then exsanguinated, or occasionally anaesthetized with nembutal (about 60–80 mg/kg i.v.) and killed by opening the thorax. The thorax aorta is removed, freed of adhering connective tissue, divided into 1.5 mm-wide ring segments, and placed individually, under an initial loading of about 3.5 g, in 10 ml organ baths containing 5% CO$_2$/95% O$_2$-gassed Krebs-Henseleit nutrient solution of the following composition: 119 mmol/l NaCl; 2.5 mmol/l CaCl$_2$×2H$_2$O; 1.2 mmol/l KH$_2$PO$_4$; 10 mmol/l glucose; 4.8 mmol/l KCl; 1.4 mmol/l MgSO$_4$×7H$_2$O and 25 mmol/NaHCO$_3$ which has been brought to 37° C.

The contractions are recorded isometrically by Statham UC2 cells via bridge amplifiers (ifd Mülheim or DSM Aalen) and digitalized by means of an analog/digital converter (System 570, Keithley, Munich), and evaluated. Agonist dose-effect curves (DEC) are plotted hourly. For each DEC, 3 or 4 individual concentrations are administered to the baths at 4 minute intervals. Once the DEC and subsequent washing cycles (16 times in each cafe for about 5 sec/min with the abovementioned nutrient solution) have finished, a 28-minute rest or incubation phase follows within which, as a rule, the contractions once again achieve the starting value.

The height of what is usually the 3rd DEC is used as the reference quantity for evaluating the test substance which is to be investigated in subsequent rounds, which substance is administered to the baths in successively increasing dosages for each of the following DECs from the beginning of the incubation time. In this procedure, each aorta ring is always stimulated with the same agonist for the whole of the day. Agonists and their standard concentrations (volume administered per individual dose=100 µl):

KCl 22.7;32.7;42.7;52.7 mmol/l

Noradrenaline $3\times10^{-9}; 3\times10^{-8}; 3\times10^{-7}; 3\times10^{-6}$ g/ml
Serotonin $10^{-8}; 10^{-7}; 10^{-6}; 10^{-5}$ g/ml
B-HT 920 $10^{-7}; 10^{-6}; 10^{-5}$ g/ml
Methoxamine $10^{-7}; 10^{-6}; 10^{-5}$ g/ml
Angiotensin II $3\times10^{-9}; 10^{-8}; 3\times10^{-8}; 10^{-7}$ g/ml The effect obtained at the 3rd (=submaximal) agonist concentration is in each case used for calculating the $IC_{50}$ (concentration at which the substance under investigation causes a 50% inhibition).

The compounds according to the invention inhibit the angiotensin II-induced contraction of the isolated rabbit aorta in a dose-dependent manner. Contraction induced by potassium-depolarization or other agonists was either not inhibited at all or only inhibited weakly at high concentrations.

Measurements of blood pressure in the angiotensin II-infused rat

Male Wistar rats (Moellegaard, Copenhagen, Denmark) having a body weight of from 300–350 g are anaesthetized with thiopental (100 mg/kg i.p.). Following tracheotomy, a catheter for measuring blood pressure is introduced into the femoral artery, while a catheter for infusing angiotensin II and a catheter for substance administration are introduced into the femoral veins. After administering the ganglionic blocking agent pentolinium (5 mg/kg i.v.), the angiotensin II infusion (0.3 μg/kg/min) is started. As soon as the blood pressure values have reached a stable plateau, the test substances are administered either intravenously, or else orally as a suspension or solution in 0.5% Tylose.

Determination of the antihypertensive activity in conscious hypertensive rats

The oral anti-hypertensive activity of the compounds according to the invention was tested in conscious rats in which stenosis of the renal artery had been induced unilaterally by surgery. The latter was done by constricting the right renal artery using a silver crocodile clip having an internal clearance of 0.18 mm. In this form of hypertension, the activity of renin in the plasma is increased over the first six weeks following intervention.

The arterial blood pressure of these animals was measured in a non-operative manner using the "tail cuff" at defined time intervals after substance administration. The substances to be tested were administered in various doses intragastrically ("orally") in suspension in Tylose via a stomach tube. The compounds according to the invention lower the arterial blood pressure of the hypertensive rats in doses which are clinically relevant.

In addition, the compounds according to the invention inhibit the specific binding of radioactive angiotensin II in a concentration-dependent manner.

Interaction of the compounds according to the invention with the angiotensin II receptor on membrane fractions from the adrenal cortex (cattle)

Adrenal cortices from cattle (ACC), which are freshly removed and carefully freed from medulla and from capsule, are comminuted in sucrose solution (0.32M) to form a coarse membrane homogenate using an Ultra-Turrax (Janke & Kunkel, Staufen i.B.) and partially purified into membrane fractions in two centrifugation steps.

The investigations of receptor binding are carried out on partially purified membrane fractions of bovine ACC using radioactive angiotensin II in an assay volume of 0.25 ml, the itemized content of which is the partially purified membranes (50–80 μg), $^3$H-angiotensin II (3–5 nM), test buffer solution (50 mM Tris, pH 7.2, 5 mMMgCl$_2$) and the substances under investigation. After an incubation period of 60 min at room temperature, the unbound radioactivity of the samples is separated off using moistened glass fibre filters (Whatman GF/C) and the bound radioactivity is measured spectrophotometrically in a scintillation cocktail after washing the protein with ice-cold buffer solution (50 mM Tris/HCl, pH 7.4, 5% PEG 6000). The raw data were analysed using computer programs to obtain $K_i$ and $IC_{50}$ values ($K_i$:$IC_{50}$ values corrected for the radioactivity used; $IC_{50}$ values: concentration at which the substance under investigation brings about a 50% inhibition of the specific binding of the radioligand).

Investigation of the inhibition of the proliferation of smooth muscle cells by the compounds according to the invention In order to ascertain the anti-proliferative effect of the compounds, smooth muscle cells are used which are isolated from rat aortas using the media-explant technique [R. Ross, J. Cell. Biol. 50, 172, 1971]. The cells are sown in appropriate culture dishes, as a rule 96-well plates, and cultivated at 37° C. in 5% $CO_2$ for 2–3 days in medium 199 containing 7.5% FCS and 7.5% NCS, 2 mM L-glutamine and 15 mM HEPES, pH 7.4. After that, the cells are synchronized by removing serum for 2–3 days, and then stimulated to grow with serum or other factors. Test compounds are added at the same time. After 16–20 hours, 1 μCi of $^3$H-thymidine is added and, after a further 4 hours, incorporation of this substance into the TCA-precipitable DNA of the cells is determined. In order to determine the $IC_{50}$ values, the concentration of active compound is computed which, with sequential dilution of the active compound, brings about half-maximal inhibition of the thymidine incorporation elicited by 10% FCS.

The novel active compounds can be converted, in a known manner, into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present at a concentration of from about 0.5 to 90% by weight of the total mixture, i.e. in quantities which are sufficient to achieve the given dosage scope.

The formulations are, for example, prepared by extending the active compounds with solvents and/or excipients, where appropriate using emulsifying agents and/or dispersing agents, it being possible, e.g. when using water as a diluent, to use organic solvents as auxiliary solvents where appropriate.

Administration is effected in a customary manner, preferably orally or parenterally, in particular perlingually or intravenously.

For parenteral applications, solutions of the active compound can be employed which make use of appropriate liquid carrier materials.

In general, it has been found to be advantageous in the case of intravenous administration to administer quantities of from about 0.001 to 1 mg/kg, preferably about 0.01 to 0.5 mg/kg, of body weight in order to obtain effective results, and, in the case of oral administration, the dosage amounts to about 0.01 to 20 mg/kg, preferably 0.1 to 10 mg/kg, of body weight.

Despite this, it can, where appropriate, be necessary to diverge from the said quantities, depending on the body weight and the nature of the route of administration, on the individual response to the medicament, on the nature of its formulation, and on the time point or interval at which administration is effected. Thus, it can be sufficient in some cases to make do with less than the aforesaid lowest quantity, while in other cases the said upper limit must be exceeded. When relatively large quantities are being administered, it can be advisable to divide these up into several smaller doses to be given over the course of the day.

Starting compounds

EXAMPLE I

2-Cyclopropyl-5,7-dimethyl-3-(6-bromopyridin-3-ylmethyl)imidazo[4,5-b]pyridine

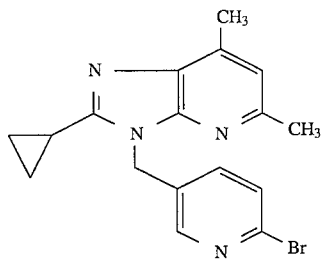

255 mg (6.4 mmol) of sodium hydride and 994 mg (5.3 mmol) of 2-cyclopropyl-5,7-dimethylimidazo[4,5-b]pyridine are stirred at 0° C. for 2 h in 15 ml of dimethyl sulphoxide. After adding 2 g (7.97 mmol) of 2-bromo-5-bromomethylpyridine, the mixture is stirred at room temperature overnight. The reaction mixture is diluted with water and washed twice with ethyl acetate; the combined organic phases are washed with water and sodium chloride solution, dried over sodium sulphate and then chromatographed on 150 g of silica gel using ethyl acetate/petroleum ether mixtures 1:2→1:0 to yield 1.32 g of the title compound.

Yield: 69.7% of theory $R_f$=0.45 (silica gel 60, ethyl acetate)

EXAMPLE II (S)-N-(1-Ethoxycarbonyl-2-methyl-prop-1-yl)-N-(6-bromopyridin-3-ylmethyl)-amine

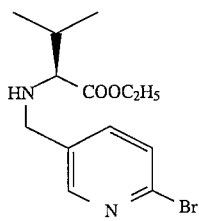

A solution of 4.77 g (25.65 mmol) of 6-bromo-3-pyridinecarboxaldehyde, 4.66 g (25.65 mmol) of L-valine ethyl ester hydrochloride and 4.24 g (51.3 mmol) of sodium acetate in 400 ml of methanol is stirred for 30 min together with 25 g of 4A molecular sieve. After adding 3.22 g (51.3 mmol) of sodium cyanoborohydride, the mixture is stirred at room temperature overnight, adjusted to pH=2 with dilute hydrochloric acid, then adjusted to pH 10 with sodium carbonate and filtered with suction through kieselguhr. The solution is diluted with water and washed three times with ethyl acetate; the combined organic phases are washed with sodium chloride solution, and then dried over sodium sulphate and chromatographed on 350 g of silica gel using ethyl acetate/toluene mixtures (1:20→1:10) to give 1.98 g of the title compound.

Yield: 24% of theory $R_f$=0.1 (silica gel 60, ethyl acetate/toluene 1:20)

EXAMPLE III (S)-N-(1-Ethoxycarbonyl-2-methyl-prop-1-yl)-N-(3-oxo-2-propyl-heptanoyl)-N-(6-bromopyridin-3-ylmethyl)-amine

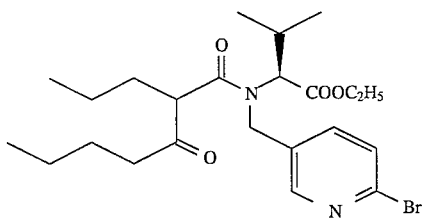

1.93 g (6.12 mmol) of the compound from Example II, 1.11 ml (9.2 mmol) of valeryl chloride, 1.69 ml (12.2 mmol) of triethylamine and a spatula tip of 4-dimethylaminopyridine are stirred at 0° C. in 10 ml of dichloromethane. After 18 h, further quantities of 1.69 ml of triethylamine and 1.11 ml of valeryl chloride are added and the mixture is stirred at room temperature overnight. The reaction mixture is diluted with water and washed with dichloromethane; the organic phases are then washed with water and dried over sodium sulphate and chromatographed on 150 g of silica gel using ethyl acetate/toluene 1:10 to give 1.13 g of the title compound.

Yield: 45.5% of theory $R_f$=0.31 (silica gel 60, ethyl acetate/toluene 1:10)

EXAMPLE IV (S)-N-(6-Bromopyridin-3-ylmethyl)-N-(1-methoxycarbonylbut-1-yl)amine

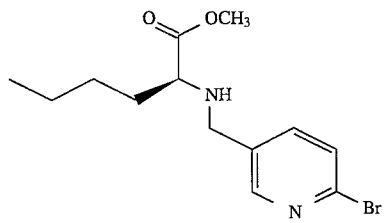

1.48 g (13.2 mmol) of potassium tert-butylate are added to a solution of 2.18 g (12 mmol) of methyl (S)-2-aminohexanoate hydrochloride and 1.66 ml of triethylamine in 20 ml of DME and 15 ml of DMF under argon. After stirring at 20° C. for 1 h, a solution of 3.01 g (12 mmol) of 2-bromo-5-bromomethylpyridine in 15 ml of DMF is injected and the mixture is stirred for 16 h. Subsequently, the solvent is distilled off in vacuo and the residue is taken up in dichloromethane/water; the organic phase is then dried over sodium sulphate and, after concentrating, purified on silica gel using petroleum ether/ethyl acetate (4:1).

Yield: 1.64 g (46% of theory)

$R_f$=0.32 (petroleum ether/ethyl acetate=3:1)

EXAMPLE V (S)-1-(6-Bromopyridin-3-ylmethyl)-3,5-dibutyl-imidazolidine-2,4-dione

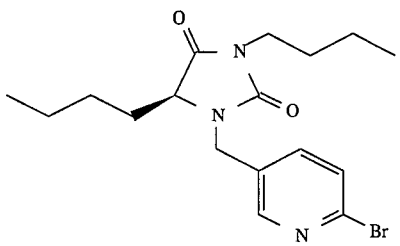

A solution of 900 mg (2.84 mmol) of the compound from Example IV and 845 mg (8.52 mmol) of butyl isocyanate in 20 ml of ethyl acetate is heated under reflux for 16 h. Subsequently, 20 ml of 6M hydrochloric acid are added, the mixture is stirred at 60° C. for 1 h, diluted with 30 ml of ethyl acetate, and then washed with 20 ml of water. The organic phase is separated off, and then dried over sodium sulphate and concentrated to give 1.1 g of crude product which can be used for further reaction without purification.

$R_f$=0.66 (toluene/ethyl acetate/glacial acetic acid=10:30:1)

EXAMPLE VI

N-(6-Bromopyridin-3-ylmethyl)-N-butylamine

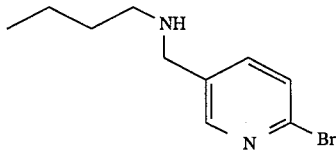

A solution of 2 g (7.97 mmol) of 2-bromo-5-bromomethylpyridine and 2.91 g (39.85 mmol) of n-butylamine in 20 ml of dioxane is heated under reflux for 2 h. Subsequently, the solvent is removed in vacuo and the residue is taken up in ethyl acetate/dichloromethane, which is then washed with water and a saturated solution of sodium chloride. The organic phase is dried over sodium sulphate and concentrated, and the residue is purified on silica gel using dichloromethane/methanol (95:5).

Yield: 1.42 g (73% of theory)

$R_f$=0.49 (dichloromethane/methanol=95:5)

EXAMPLE VII (S)-N-(6-Bromopyridin-3-ylmethyl)-N-butyl-N'-(1-methoxycarbonyl-2-methylbutyl)urea

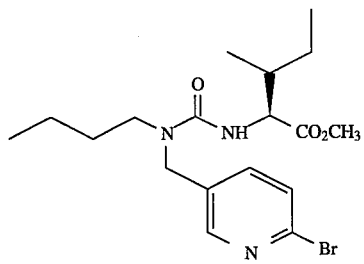

A solution of 0.73 g (3 mmol) of the compound from Example VI in 5 ml of ethyl acetate is added at 0° C. to a solution of 0.93 g (2.16 mmol) of (S)-isoleucine methyl ester isocyanate (prepared by reacting (S)-isoleucine methyl ester hydrochloride with trichloromethyl chloroformate in toluene at 120° C.) in 10 ml of ethyl acetate, and the mixture is stirred at this temperature for 30 min. Subsequently, the reaction mixture is washed successively with dilute hydrochloric acid, water and saturated solutions of sodium hydrogen carbonate and sodium chloride, and the organic phase is then concentrated and the residue purified on silica gel using petroleum ether/ethyl acetate (2:1).

Yield: 658 mg (74% of theory)

$R_f$=0.53 (petroleum ether/ethyl acetate=1:1)

EXAMPLE VIII

Ethyl 2-{[N-(6-bromopyridin-3-ylmethyl)-N-propyl]amino}pyridine-3-carboxylate

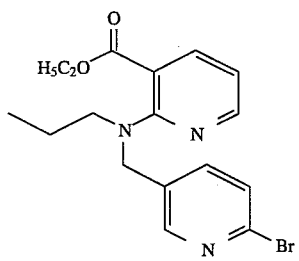

3.2 ml of a 1.6N solution of n-butyllithium are added at −20° C. to a solution of 0.87 g (5.4 mmol) of hexamethyldisilazane in 5.5 ml of THF. The solution prepared in this way is added dropwise at from −10° C. to 0° C. to a solution of 1.07 g (5.13 mmol) of ethyl 2-propylaminopyridine-3-carboxylate and 1.25 g of 1,3-dimethyltetrahydro-2(1H)-pyrimidinone (DMPU) in 4 ml of THF. After stirring at this temperature for 10 min, 2 g (8 mmol) of 2-bromo-5-bromomethylpyridine dissolved in 12 ml of THF are added slowly dropwise. After removing the cooling bath, the mixture is stirred at 20° C. for 36 h. After that, 2 drops of conc. hydrochloric acid are added, the solvent is removed in vacuo, and the residue is taken up in ethyl acetate, which is then washed three times with water. The organic phase is dried over sodium sulphate and concentrated, and the residue is purified on silica gel using petroleum ether/ethyl acetate (20:1).

Yield: 1.14 g (59% of theory)

$R_f$=0.35 (petroleum ether/ethyl acetate=5:1)

Preparation Examples

EXAMPLE 1

2-Cyclopropyl-5,7-dimethyl-3-{6-[2-(1-triphenyl-methyltetrazol-5-yl)-phenyl]-pyridin-3-yl-methyl}imidazo-[4,5-b]pyridine

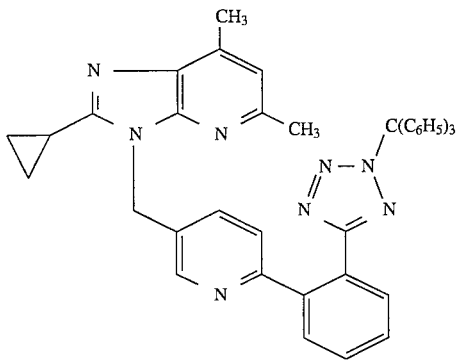

A suspension of 1.3 g (3.64 mmol) of the compound from Example I, 1.73 g (4.0 mmol) of 3-(2'-triphenylmethyl-2'H-tetrazol-5'-yl)phenylboronic acid, 772 mg (7.28 mmol) of sodium carbonate, 420 mg (0.36 mmol) of tetrakis(triphenylphosphine) palladium, 4 ml of methanol, 4 ml of water and 40 ml of toluene is heated under reflux overnight and under an argon atmosphere. The reaction mixture is washed with water and sodium chloride solution, dried over sodium sulphate, and chromatographed on 200 g of silica gel using ethyl acetate/petroleum ether (1:1) to give 1.53 g of the title compound.

Yield: 63.2% of theory $R_f$=0.11 (silica gel 60, ethyl acetate/petroleum ether 1)

EXAMPLE 2

2-Cyclopropyl-5,7-dimethyl-3-{6-[2-(1H-tetrazol-5-yl)phenyl]pyridin-3-yl-methyl}imidazo[4,5-b]pyridine

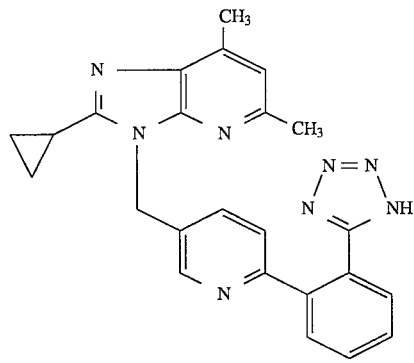

0.75 g (1.13 mmol) of the compound from Example 1 and 0.1 ml of concentrated hydrochloric acid are stirred at room temperature overnight in 15 ml of methanol. The reaction mixture is diluted with water and washed three times with ethyl acetate; the combined organic phases are washed with water and sodium chloride solution and then dried over sodium sulphate and chromatographed on 100 g of silica gel using dichloromethane/methanol mixtures (20:1→0:1) to give 175 mg of the title compound.

Yield: 36.3 g of theory $R_f$=0.50 (silica gel 60, acetonitrile/water 5:1)

MS (FAB): 423 (M+H), 445 (M+Na)

The compounds listed in Table 1 are obtained in analogy with the instructions in Examples 1 and 2.

TABLE 1

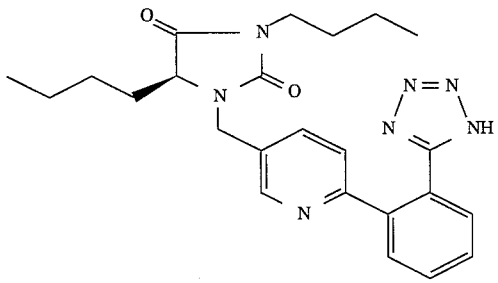

| Ex. No. | V | MS (FAB) |
|---|---|---|
| 3 | ![Cl-substituted pyrrole with CHO] | 444/446 (M+Na) 422/424 (M+1) |
| 4 | ![structure with COOC2H5] | 549 (M+1) |
| 5 | ![structure with COOC2H5] | 465 (M+1) |

EXAMPLE 6

(S)-3,5-Dibutyl-1-{6-[2-(1H-tetrazol-5-yl)phenyl]pyridin-3-ylmethyl}-imidazolidine-2,4-dione 272 mg of tetrakis(triphenylphosphine)palladium(NaH), 7.1 ml of 2 M sodium carbonate solution, 538 mg (2.83 mmol) of 2-(tetrazol-5'-yl)phenylboronic acid and 1 ml of ethanol are added successively to a solution of 1.1 g (2.36 mmol) of the compound from Example V in 20 ml of DME, and the mixture is heated under reflux for 16 h. After cooling down, the reaction mixture is filtered with suction through kieselguhr, followed by subsequent washing with methanol; the solvent is then removed and the residue is purified on silica gel using toluene/ethyl acetate/glacial acetic acid (35:5:1).

Yield: 917 mg (87% of theory)

$R_f$=0.22 (toluene/ethyl acetate/glacial acetic acid= 20:20:1)

EXAMPLE 7

(S)-N-Butyl-N-{6-[2-(1H-tetrazol-5-yl)phenyl]pyridin-3-ylmethyl}-N'-(1-methoxycarbonyl-2-methylbutyl)urea

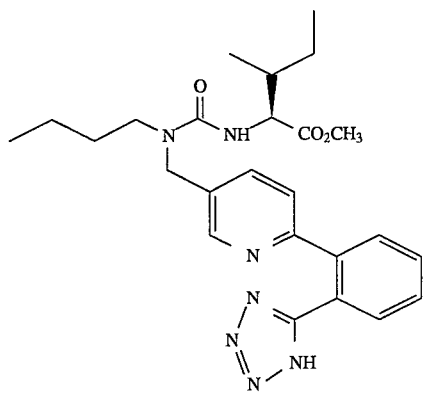

The title compound is obtained from 658 mg (1.59 mmol) of the compound from Example VII and 363 mg (1.9 mmol) of 2-(tetrazol-5'-yl)phenylboronic acid in analogy with the instructions in Example 6.

Yield: 123 mg (16% of theory)

$R_f$=0.52 (toluene/ethyl acetate/glacial acetic acid= 20:20:1)

EXAMPLE 8

(S)-N-(1-Carboxy-2-methyl-prop-1-yl)-N-3-oxo-2-propylheptanoyl-N-{6-[2-(1H-tetrazol-5-yl)phenyl]pyridin-3 ylmethyl}amine

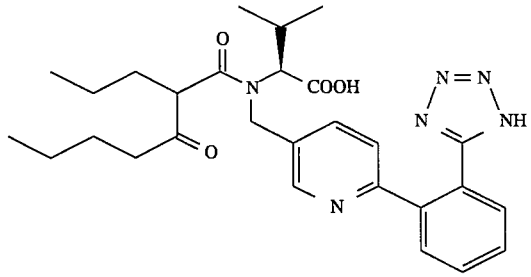

A solution consisting of 50 mg (0.9 mmol) of the compound from Example 4 in ethanol and 2.3 ml of a 0.1N potassium hydroxide solution is stirred at 20° C. overnight. The mixture is then acidified with dilute hydrochloric acid and washed with ethyl acetate; the combined organic phases are dried over sodium sulphate and concentrated.

Yield: 73% of theory $R_f$ (acetonitrile/water, silica gel 10:1)=0.36

EXAMPLE 9

(S)-N-Butyl-N-{6-[2-(1H-tetrazol-5-yl)phenyl]pyridin-3-ylmethyl}-N'-(1-carboxy-2-methylbutyl)urea

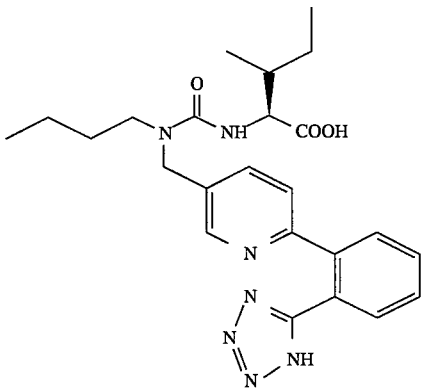

The title compound is obtained from 110 mg (0.23 mmol) of the compound from Example 7 in analogy with the instructions in Example 8.

Yield: 43 mg (40% of theory)

$R_f$=0.18 (toluene/ethyl acetate/glacial acetic acid= 20:20:1)

EXAMPLE 10

Ethyl 2-{N-propyl-N-[6-[2-(1H-tetrazol-5-yl)phenyl]pyridin-3-ylmethyl]amino}pyridine-3-carboxylate

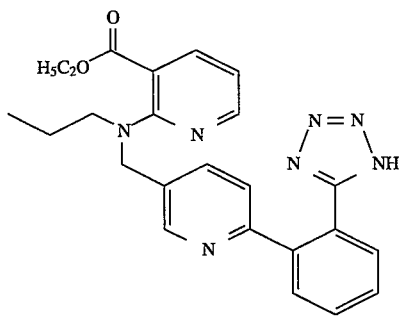

The title compound is obtained from 1.14 g (3 mmol) of the compound from Example VIII and 0.69 g (3.61 mmol) of 2-(tetrazol-5'-yl)phenylboronic acid in analogy with the instructions in Example 6.

Yield: 807 mg (60% of theory)

$R_f$=0.47 (toluene/ethyl acetate/glacial acetic acid= 20:20:1)

EXAMPLE 11

2-(N-Propyl-N-{6-[2-(1H-tetrazol-5-yl)phenyl]pyridin-3-ylmethyl]amino}pyridine-3-carboxylic acid

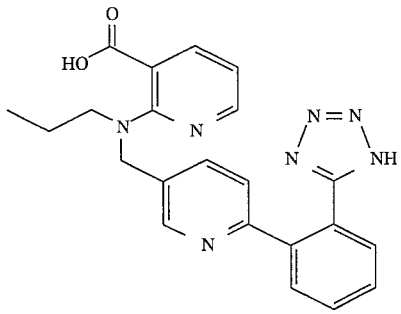

The title compound is obtained from 320 mg (0.72 mmol) of the compound from Example 10 in analogy with the instructions in Example 8.

Yield: 91 mg (31% of theory)

$R_f$=0.18 (toluene/ethyl acetate/glacial acetic acid= 20:20:1)

EXAMPLE 12

2-Cyclopropyl-5,7-dimethyl-3-{6-[2-(1H-tetrazol-5-yl)phenyl]pyridin-3-ylmethyl}-imidazo[4,5-b]pyridine potassium salt

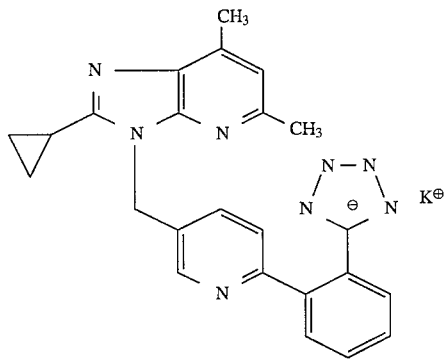

9.4 ml (0.31 mmol) of the compound from Example 2 and 30.6 mg (0.31 mmol) of potassium hydrogen carbonate are stirred at room temperature for 2 h in 6 ml of methanol, 0.6 ml of water and 3 ml of tetrahydrofuran. The mixture is concentrated in vacuo and the residue is lyophilized and dried in vacuo over phosphorus pentoxide to give 4 mg of the title compound.

Yield: 95.1% of theory

MS (FAB): 423 (M+H), 445 (M+Na), 461 (M+K)

The compounds listed in Table 2 are obtained in analogy with the instructions in Example 12.

TABLE 2

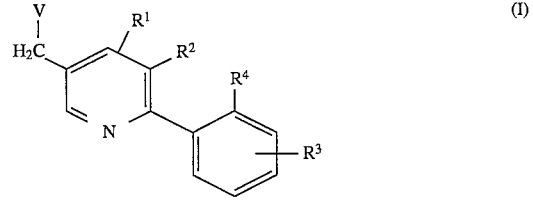

| Ex. No. | V | MS (FAB) |
|---|---|---|
| 13 | ![structure with Cl, N, CHO] | 444/446 (M+Na) 422/424 (M+H) 460/462 (M+K) |
| 14 | ![structure with COOC2H5] | 587 (M+K) 549 (M+H) |
| 15 | ![structure with COOK] | |
| 16 | ![structure with COOK] | |

We claim:

1. A substituted monopyridylmethyl derivative of the formula

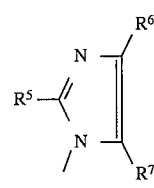

(I)

in which

V represents a radical of the formula

[structure with $R^5$, $R^6$, $R^7$]

in which $R^5$ denotes straight-chain or branched alkyl having up to 10 carbon atoms which is optionally substituted by cycloalkyl having 3 to 6 carbon atoms, by hydroxyl, or by straight-chain or branched alkoxy or alkylthio having in each case up to 6 carbon atoms, or denote cycloalkyl having 3 to 6 carbon atoms, $R^6$ denotes halogen, $R^7$ denotes formyl, carboxyl, straight-chain or branched alkoxycarbonyl having up to 6 carbon atoms, or straight-chain or branched alkyl having up to 6 carbon atoms which is optionally substituted by hydroxyl, $R^1$, $R^2$ and $R^3$ are identical or different and represent hydrogen, halogen, cyano, nitro, trifluoromethyl or amido, or represent straight-chain or branched alkyl or alkoxycarbonyl having up to 6 carbon atoms, $R^4$ represents a group of the formula —CO—$R^{14}$, —SO$_2$$R^{15}$, —CO—NR$^{16}$R$^{17}$, —NH—SO$_2$R$^{18}$ or —SO$_2$NR$^{19}$R$^{20}$, in which $R^{14}$ denotes hydroxyl or straight-chain or branched alkoxy having up to 6 carbon atoms, $R^{15}$ denotes hydroxyl, trifluoromethyl, straight-chain or branched alkoxy or alkyl having in each case up to 6 carbon atoms, phenyl or benzyl which are optionally substituted identically or differently up to 2 times by halogen, trifluoromethyl or straight-chain or branched alkyl having up to 4 carbon atoms, $R^{16}$ and $R^{17}$ are identical or different and denote hydrogen, cycloalkyl having 3 to 8 carbon atoms, or straight-chain or branched alkyl having up to 8 carbon atoms which is optionally substituted by phenyl, or $R^{16}$ denotes hydrogen and $R^{17}$ denotes the group —SO$_2$R$^{15}$, in which $R^{15}$ has the abovementioned meaning, $R^{18}$ as the abovementioned meaning of $R^{15}$ and is identical to or different from the latter, $R^{19}$ and $R^{20}$ have the abovementioned meaning of $R^{16}$ and $R^{17}$ and are identical to or different from the latter, or $R^{19}$ denotes hydrogen or straight-chain or branched alkyl having up to 4 carbon atoms, and $R^{20}$ has the abovementioned meaning of $R^{15}$ and is identical to or different from the latter, or $R^4$ represents a radical of the formula

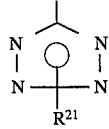

in which $R^{21}$ denotes hydrogen or straight-chain or branched alkyl having up to 8 carbon atoms which is optionally substituted by straight-chain or branched acyl having up to 6 carbon atoms, or denotes the triphenylmethyl group, or a salt thereof.

2. A substituted monopyridylmethyl derivative according to claim 1, wherein $R^5$ denotes straight-chain or branched alkyl having in each case up to 8 carbon atoms which is optionally substituted by cyclopropyl, cyclopentyl, cyclohexyl or hydroxyl, or by straight-chain or branched alkoxy or alkylthio having in each case up to 4 carbon atoms, or denote cyclopropyl, cyclopentyl or cyclohexyl, $R^6$ denotes fluorine, chlorine or bromine, $R^7$ denotes formyl, carboxyl, straight-chain or branched alkoxycarbonyl having up to 4 carbon atoms, or straight-chain or branched alkyl having up to 4 carbon atoms which is optionally substituted by hydroxyl, $R^1$, $R^2$ and $R^3$ are identical or different and represent hydrogen, fluorine, chlorine, bromine, trifluoromethyl or amido, or represent straight-chain or branched alkyl or alkoxycarbonyl having in each case up to 4 carbon atoms, $R^4$ represents a group of the formula —CO—$R^{14}$, —SO$_2$R$^{15}$, —CO—NR$^{16}$R$^{17}$, —NH—SO$_2$R$^{18}$ or —SO$_2$NR$^{19}$R$^{20}$, in which $R^{14}$ denotes hydroxyl or straight-chain or branched alkoxy having up to 4 carbon atoms, $R^{15}$ denotes straight-chain or branched alkyl having up to 4 carbon atoms, benzyl, trifluoromethyl or p-tolyl, $R^{16}$ and $R^{17}$ are identical or different and denote hydrogen, cyclopropyl, cyclopentyl or cyclohexyl, or straight-chain or branched alkyl having up to 6 carbon atoms which is optionally substituted by phenyl, or $R^{16}$ denotes hydrogen, and $R^{17}$ denotes the group —SO$_2$R$^{15}$, in which $R^{15}$ has the abovementioned meaning, $R^{18}$ has the abovementioned meaning of $R^{15}$ and is identical to or different from the latter, $R^{19}$ and $R^{20}$ have the abovementioned meaning of $R^{16}$ and $R^{17}$ and are identical to or different from the latter, or $R^{19}$ denotes hydrogen or methyl, $R^{20}$ has the abovementioned meaning of $R^{15}$ and is identical to or different from the latter, or $R^4$ represents a radical of the formula

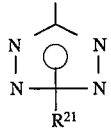

in which $R^{21}$ denotes hydrogen or straight-chain or branched alkyl having up to 6 carbon atoms which is optionally substituted by straight-chain or branched acyl having up to 4 carbon atoms, or denotes the triphenylmethyl group, or a salt thereof.

3. A substituted monopyridylmethyl derivative according to claim 1, wherein $R^5$ denotes straight-chain or branched alkyl having up to 6 carbon atoms which is optionally substituted by cyclopropyl or hydroxyl, or by straight-chain or branched alkoxy or alkylthio having in each case up to 3 carbon atoms, or denote cyclopropyl, chlorine or iodine, $R^6$ denotes fluorine, chlorine or bromine, $R^7$ denotes formyl, carboxyl, straight-chain or branched alkoxycarbonyl having up to 3 carbon atoms, or straight-chain or branched alkyl-having up to 4 carbon atoms which is optionally substituted by hydroxyl, $R^1$, $R^2$ and $R^3$ are identical or different and represent hydrogen, fluorine, chlorine, bromine or methyl, $R^4$ denotes a group of the formula $-CO-R^{14}$, $-SO_2R^{15}$, $-CO-NR^{16}R^{17}$, $-NH-SO_2R^{18}$ or $-SO_2NR^{19}R^{20}$, in which $R^{14}$ denotes hydroxyl or straight-chain or branched alkoxy having up to 3 carbon atoms, $R^{15}$ denotes methyl, trifluoromethyl, benzyl or p-tolyl, $R^{16}$ and $R^{17}$ are identical or different and denote hydrogen, cyclopropyl or cyclopentyl, or straight-chain or branched alkyl having up to 4 carbon atoms which is optionally substituted by phenyl, $R^{16}$ denotes hydrogen, and $R^{17}$ denotes the, group $-SO_2-R^{15}$, in which $R^{15}$ has the abovementioned meaning, $R^{18}$ has the abovementioned meaning of $R^{15}$ and is identical to or different from the latter, $R^{19}$ and $R^{20}$ have the abovementioned meaning of $R^{16}$ and $R^{17}$ and are identical to or different from the latter, or $R^{19}$ denotes-hydrogen or methyl, and $R^{20}$ has the abovementioned meaning of $R^{15}$ and is identical to or different from the latter, or $R^4$ represents the tetrazolyl radical of the formula

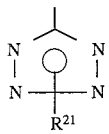

in which $R^{21}$ denotes hydrogen or straight-chain or branched alkyl having up to 4 carbon atoms which is optionally substituted by straight-chain or branched acyl having up to 4 carbon atoms, or denotes the triphenylmethyl group, or a salt thereof.

4. A substituted monopyridylmethyl derivative according to claim 1, wherein $R^5$ denotes straight-chain or branched alkyl having up to 6 carbon atoms, or cyclopropyl, $R^6$ denotes fluorine, chlorine or bromine, $R^7$ denotes formyl, carboxyl, methoxycarbonyl or ethoxycarbonyl, or hydroxymethyl, $R^1$, $R^2$ and $R^3$ represent hydrogen, $R^4$ represents a tetrazolyl radical of the formula

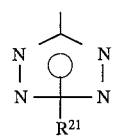

in which $R^{21}$ denotes hydrogen or the triphenylmethyl group, or a salt thereof.

5. A substituted monopyridyl derivative according to claim 1 wherein such compound is 5-butyl-3-chloro-2-formyl-{6-[2-(1H-tetracol-5-yl)phenyl]pyridin-3-ylmethyl}imidazol of the formula

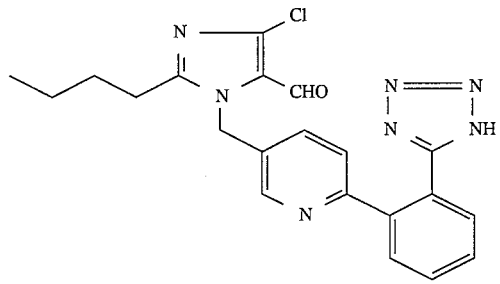

and salts thereof.

6. A composition for the treatment of arterial hypertension and atherosclerosis comprising an amount effective therefore of a compound or salt thereof according to claim 1 and a pharmacologically acceptable diluent.

7. The method of treating arterial hypertension and atherosclerosis in a patient in need thereof which comprises administering to such patient an amount effective therefore of a compound or salt thereof according to claim 1.

* * * * *